US007932051B2

(12) United States Patent
Geijp et al.

(10) Patent No.: US 7,932,051 B2
(45) Date of Patent: Apr. 26, 2011

(54) BLOOD AND URINE TEST

(75) Inventors: Edith Magda Lucia Geijp, Pijnacker (NL); Jacobus J. Stark, Rotterdam (NL)

(73) Assignee: R-Biopharm AG, Darmstadt (DE)

( * ) Notice: Subject to any disclaimer, the term of this patent is extended or adjusted under 35 U.S.C. 154(b) by 1021 days.

(21) Appl. No.: 10/570,882

(22) PCT Filed: Sep. 6, 2004

(86) PCT No.: PCT/EP2004/009948
§ 371 (c)(1),
(2), (4) Date: Sep. 14, 2006

(87) PCT Pub. No.: WO2005/024048
PCT Pub. Date: Mar. 17, 2005

(65) Prior Publication Data
US 2007/0031915 A1    Feb. 8, 2007

(30) Foreign Application Priority Data
Sep. 11, 2003 (EP) .................................. 03102730

(51) Int. Cl.
C12Q 1/18 (2006.01)
G01N 33/569 (2006.01)
(52) U.S. Cl. .................. 435/32; 435/7.32; 435/7.34
(58) Field of Classification Search ................. None
See application file for complete search history.

(56) References Cited

U.S. PATENT DOCUMENTS

| | | | |
|---|---|---|---|
| 4,766,063 A * | 8/1988 | Boussemaer | 435/5 |
| 5,536,645 A | 7/1996 | Jay | |
| 6,867,015 B1 * | 3/2005 | Langeveld et al. | 435/29 |

FOREIGN PATENT DOCUMENTS

| | | |
|---|---|---|
| EP | 0 005 891 | 12/1979 |
| EP | 0 702 087 | 1/2000 |
| GB | 1 467 439 | 3/1977 |
| JP | 54-159295 | 12/1979 |
| JP | 63 192387 | 8/1988 |
| JP | 5-33897 | 2/1993 |

OTHER PUBLICATIONS

Srivastava et al. Insulin Constitutively Secreted by Beta-Cells is Necessary for Glucose-Stimulated Insulin Secretion; Diabetes, vol. 52 (2003) pp. 2049-2056.*
Berdicevsky, I and Grosswicz, N. Reversal by Calcium Ions of the Growth Inhibition of Debarymyces Nicotianae Caused by Antifungal Polyene Antibiotics; Antimicrobial Agents and Chemotherapy, vol. 2, No. 1 (1972) pp. 1-7.*
Miles, A.A. And Maskell, J.P. The Neutralization of Antibiotic Action by Metallic Cations and Iron Chelators; Journal of Antimicrobial Chemotherapy, vol. 17 (1986) pp. 481-487.*
Berkowitz, F.E. Antibiotic Resistance in Bacteria; Southern Medical Journal, vol. 88, No. 8 (1995) pp. 797-804.*
Somkuti et al. Native Promoter-Plasmid Vector System for Heterologous Cholesterol Oxidase Synthesis in *Streptococcus thermophilus*; Plasmid, vol. 33 (1995) pp. 7-14.*
Jurado et al. Influence of Divalent Cations on the Growth and Morphology of *Bacillus stearothermophilus*; Journal of General Microbiology, vol. 133 (1987) pp. 507-513.*
International Search Report Feb. 4, 2005.
Mercedes Lopez et al; "Influence of recovery conditions on apparent heat resistance of *Bacillus stearothermophilus* spores"; International Journal of Food Science and Technology, Aug. 4, 1997, vol. 32, pp. 305-311.
A. Sikes et al; "Recover of Heat-stressed Spores of *Bacillus stearothermophilus* on Solid Media Containing Calcium- and Magnesium-deficient Agar"; Journal of Food Protection, 1993, vol. 56, No. 8, pp. 706-709.

* cited by examiner

*Primary Examiner* — Rebecca E. Prouty
*Assistant Examiner* — Paul C. Martin
(74) *Attorney, Agent, or Firm* — Nixon & Vanderhye P.C.

(57) ABSTRACT

The present invention provides a test medium comprising a test microorganism, an indicator and a metal in ionized form, wherein the valence of said metal is at least 2 and the concentration of said metal is between 0.001 M and 1 M. Furthermore, there is provided a method for the determination of the presence of an antibiotic characterized in that a metal salt is added to said test medium and/or to said sample of fluid. Finally, there is provided a kit suitable for the determination of an antibiotic in a fluid.

11 Claims, No Drawings

BLOOD AND URINE TEST

This application is the U.S. national phase of international application PCT/EP2004/009948 filed 6 Sep. 2004 which designated the U.S. and claims benefit of EP 03102730.3, dated 11 Sep. 2003, the entire content of which is

FIELD OF THE INVENTION

The present invention relates to a novel method for the rapid detection of the presence or absence of antimicrobial drug residues in urine and blood.

BACKGROUND OF THE INVENTION

Antimicrobial drugs are not only applied as medication, but are also widely used as growth promoting substances in veterinary medicine. In modern farming the legal use of veterinary pharmaceuticals as feed additive is common practice. These feed additives prevent illness of the animal, enhance its growth or enhance the feed efficiency. The compounds may be added to the feed or the drinking water of the animals. In some countries administration by injections of for example growth promoting substances is allowed, thus increasing the amount of antimicrobial drugs in human food. Of course illegal use of veterinary drugs may also occur.

The presence of antimicrobial drugs in food is a growing concern among consumers. Allergic reactions and effects on the intestinal human flora caused by antibiotics are well known. Another issue is the development of resistant bacteria. It is well known that misuse of antibiotics (i.e. administration whenever this is not required on medical grounds, or incomplete courses of treatment) is the most important cause of the development of antibiotic resistance. Also, the presence of antimicrobial compounds in food leads to the increase of drug resistant bacteria. Human pathogenic bacteria may thus develop resistance to antimicrobials, which are both used as feed additive and in human medicine. Another drawback of the use of antibiotics in feed as growth promoter is that antibiotics influence the production process of fermented meat products such as sausages in a negative way, due to the inhibition of starter cultures.

Most veterinary drugs enter the human food chain through meat from slaughter animals or through animal products such as milk and eggs.

Control on the presence of antimicrobial drugs in slaughter animals, animal products and food products, is an important issue in food industry. In most countries maximum residue limits or tolerance levels for drug residues in fresh meat and meat products have been established. For compounds that are not allowed there is a zero tolerance, such substances may never be present in animal products. For most drugs a withdrawal period is determined. This is the minimal period between the last treatment and the time of slaughter. During this period drug residues decrease to a level below the maximum residue limit. However, in some instances, even after the withdrawal period too high drug concentrations may still be present in the animal. This may be caused by natural individual differences in the metabolism, or because of disturbance of the excretion process of the drug due to illness. Finally, procedures may not have been applied correctly in the withdrawal periods. In most countries the legislation concerning veterinary drug residues in food products is maintained by using an official control program. In general, governmental institutes examine a certain percentage of the slaughtered animals for the presence of veterinary drug residues. In addition, slaughterhouses or supermarkets may also examine raw meat, meat products and organs such as kidney and liver.

Although many of the most important antimicrobial drugs are excreted via the urine, urine is so far hardly used as substrate for examining the presence or absence of antimicrobial drug residues in slaughter animals. Examples of antimicrobial animal drugs, which are excreted via the urine, are B-lactams such as amoxicillin, ampicillin, penicillin G and penicillin V, tetracyclines such as chlortetracycline and oxytetracycline, aminoglycosides such as gentamycin and streptomycin, and sulfonamides such as sulfamidine.

The amount of antimicrobial compounds in urine is indicative for the levels of antimicrobial compounds in the edible part of the animal, e.g. the muscle tissue and the liver. It is easy to understand that examining urine offers enormous advantages. For many species of animals it is quite straightforward to obtain urine samples since many animals have specific points in time during which urine is excreted.

The use of urine as a sample to test the presence of antimicrobial drugs in the meat, would allow the animal to be tested before slaughtering. This offers the farmer the possibility to check if the withdrawal period was finished as expected. If not, the farmer will decide to wait a few days before transporting the animal to the slaughterhouse. The economic losses in case an animal is determined positive for antibiotics after slaughtering are high. It is quite obvious that the whole control system for detecting antimicrobial drug residues in the human food chain will be more efficient if the animals are examined prior to rather than after slaughtering.

As an alternative also blood samples of animals can be used to determine the presence or absence of antimicrobial drug residues in slaughter animals. Both urine and blood samples can of course also be obtained after slaughtering of the animal. In that case the valuable meat parts do not have to be damaged in order to obtain a sample.

Antimicrobial residues can be detected using microbial inhibition tests (e.g. agar diffusion tests). Such methods are mainly used for examining milk and meat fluid and are described in GB A 1467439, EP 0005891, DE 3613794, CA 2056581, EP 0285792 and U.S. Pat. No. 5,494,805. These descriptions all deal with ready to use tests that make use of a test organism. The test organism is mostly imbedded in an agar medium, which may contain an indicator, a buffer solution, nutrients and substances to change the sensitivity for certain antimicrobial compounds in a positive or negative way.

Suitable test organisms are strains of *Bacillus, Streptococcus* and/or *Escherdchia coli*. In general the principle of the test is that when antibacterial compounds are present in a sample in a concentration sufficient to inhibit the growth of the test organism, the color of an acid/base or redox indicator be retained, while in the absence of inhibition the growth of the test organism is accompanied by the formation of metabolites that will change the color of the indicator. The currently available test methods are suitable for the detection of antimicrobial residues in many different types of samples. The problem however with these test methods is that detection of antimicrobial residues in urine and blood is not possible due to the presence of disturbing substances. These substances interfere with the test leading to false positive results.

Some methods of preparing urine and blood samples are known. The easiest method is diluting the sample with water (at least threefold). However it is obvious that diluting of the sample leads to a loss of sensitivity with the same factor.

Adjusting the pH of each urine or blood sample to a certain value partly eliminates the differences between the samples.

In the case of urine the pH may differ considerably. These fluctuations are observed between species, between animals of the same species and from day to day for individual animals. For instance, due to differences in feed and the time required for obtaining the urine sample the pH may vary quite strongly between acidic and basic values. However, such methods cannot be used in practice, since it would be the most convenient to examine urine samples at the site of the farmer. Measuring the exact pH and titration of the sample to a certain pH value using acidic or alkaline solutions is much too complex in this situation. In this respect Erasmuson et al. (Analyst 123, 2497-2499 (1998)) have suggested the removal of bicarbonate from urine samples prior to analysis by acidic treatment to pH 5.5. The disadvantages of this approach are that many operations need to be performed such as addition of several aliquots of acid, measuring of the pH-value and allowing carbon dioxide to evolve and that the samples are diluted thereby decreasing the sensitivity. Further it was also observed that adjusting the pH does not give a satisfactory solution for the majority of the samples since false positive results still occur. Finally also by adjusting the pH, a major drawback again is the dilution of the sample.

It can be concluded that up to now no suitable test method for the detection of antimicrobial residues in urine and blood samples is available. The present methods are unreliable, time consuming and may lead to false positive results.

SUMMARY OF THE INVENTION

It is an object of the present invention to provide an improved test medium and a method for the determination of antibiotics in fluids, particularly blood and urine. Surprisingly, we have found that there is a substantial improvement attainable when applying a metal salt to the test medium.

To this end, there is provided a test medium comprising a test microorganism, an indicator and a metal in ionized form, wherein the valence of said metal is at least 2 and the concentration of said metal is between 0.001 M and 1 M.

Furthermore, there is provided a method for the determination of the presence of an antibiotic in a fluid comprising the steps of:
(a) contacting a sample of said fluid with a test medium comprising a test micro-organism and an indicator;
(b) incubating the test microorganism for a period of time to grow the test micro-organism in case no antibiotic is present in the fluid sample; and
(c) detecting growth or inhibition of growth of the test micro-organism with the indicator,
characterized in that a metal salt, wherein the valence of said metal is at least 2 and the metal salt has a solubility in water at 20° C. of at least 0.02 M, is added to said test medium and/or to said sample of fluid.

Also provided is a kit suitable for the determination of an antibiotic in a fluid comprising:
(a) at least one container at least partially filled with a test medium comprising a test microorganism and at least one indicator, and;
(b) a metal salt wherein the valence of said metal is at least 2 and the metal salt has a solubility in water at 20° C. of at least 0.02 M.
or comprising the test medium of any one of claims 1 to 3.

DETAILED DESCRIPTION OF THE INVENTION

The terms and abbreviations given below are used throughout this disclosure and are defined as follows.

The term 'antibiotic' refers to one or more substances or chemical constituents of a sample that display activity against bacteria.

The term 'fluid' refers to substances or compositions having particles that easily move and change their relative position without a separation of the mass, that easily yield to pressure and that are capable of flowing. In respect of the present invention, the term 'fluid' refers to compositions such as aqueous solutions, blood, guano, meat fluid, milk, urine and the like.

The term 'β-lactam antibiotic' refers to antibiotics that comprise a β-lactam substructure within their chemical structure and display activity against bacteria. Examples of said β-lactam antibiotics are amoxicillin, ampicillin, cefaclor, cefadroxil, cefprozil, ceftiofur, cephalexin, cephapirin, cephradine, cloxacillin, dicloxacillin, flucloxacillin, oxacillin, penicillin G, penicillin V and ticarcillin.

The term 'indicator' refers to a compound or substance that, upon changing from one state to another, provides a detectable signal such as a change in color or fluorescence.

The term 'test' refers to a method, procedure, process or reaction used to identify, characterize or quantify one or more antibiotics or antibiotic classes.

The term 'test device' refers to the components or part of the components suitable of performing tests with.

The term 'test medium' refers to a liquid or solidified suspension of test microorganisms, further optionally comprising at least one indicator and optionally comprising nutrients and buffering substances. Preferably the test medium is solidified in the form of a gel or sol by means of a gelling agent.

The term 'test microorganism' refers to a microorganism that is sensitive towards antibiotics and which is suitable for monitoring the presence or absence of its growth.

The term 'threshold' refers to the concentration value above which a given antibiotic is to be regarded as present and below which said antibiotic is to be regarded as absent. Generally, a threshold value is given for particular antibiotics in particular samples by local, regional or interregional authorities but it can also be pre-set for certain research purposes.

The term 'valence' refers to the degree of combining power of an element, such as a metal, as shown by the number of atomic weights of a univalent element (as hydrogen) with which the atomic weight of the element will combine or for which it can be substituted or with which it can be compared.

In a first aspect of the invention there is provided a test medium for the detection of antimicrobial compounds in fluids comprising one or more types of test microorganisms as detecting agents, optionally an indicator and a metal in ionized form. Unexpectedly it has been found that when a metal in ionized form is used in the test medium, the prior art problems mentioned above could be overcome with retention of the sensitivity of the test. Preferably, the valence of said metal is at least 2. Examples of such metals are aluminum, barium, beryllium, bismuth, calcium, chromium, cobalt, copper, iron, lanthanum, lead, magnesium, manganese, nickel, strontium, tin, titanium and zinc. More preferably said metal is an earth alkaline metal and/or a lanthanide. Most preferably, said metal is barium or calcium. Preferably, the concentration of said metal in said test medium is between 0.005 and 1 M, more preferably between 0.01 and 0.1 M. Suitable counter ions for the metal ion are ions that fulfill the solubility requirement. Preferred counter ions are acetate, benzoate, bromide, chloride, iodide, nitrate, nitrite and in some cases sulfate. The metal salts should have solubilities in water that allow for easy dissolution of the metal salt in the test sample or the test medium. In general said solubility in water should be equal to or higher than 0.01 M, preferably equal to or higher than 0.02 M, more preferably equal to or higher than 0.1 M, most preferably equal to or higher than 1 M. Preferred metal salts are barium bromide, barium chloride, barium iodide, barium nitrate, beryllium chloride, beryllium sulfate, calcium acetate, calcium bromide, calcium chloride, calcium iodide, calcium nitrate, magnesium chloride, magnesium sulfate, manganese chloride and zinc chloride. Most preferably the metal salt is calcium chloride.

Optionally, the test medium may also contain nutrients, stabilizers, and substances that change the sensitivity to certain antimicrobial compounds in a positive or negative way, and/or viscosity-increasing agents. Examples of substances that change the sensitivity to certain antimicrobial compounds are adenosine and antifolates like ormethoprim, tetroxoprim and trimethoprim that improve the sensitivity of the test organism towards sulfa compounds or salts of oxalic acid or hydrofluoric acid, which improve the sensitivity towards tetracycline. Cysteine may be added to diminish the sensitivity towards penicillins, when required. Examples of viscosity-increasing agents are ascorbyl methylsilanol pectinate, carbomer, carboxy-methyl cellulose, cetearyl alcohol, cetyl alcohol, cetyl esters, cocamide DEA, emulsifying wax, glucose, hydroxyethyl cellulose, hydroxypropylmethyl cellulose, lauramide DEA, linoleamide DEA, magnesium aluminum silicate, maltodextrins, PEG-8 distearate, polyacrylamide, polyvinyl alcohol, PVP/hexadecene copolymer, sodium chloride, sodium sulfate, soyamidopropyl betaine, xanthan gum and the like. Alternatively, the optional ingredients of the test medium mentioned above may also be added exogenously.

Optionally, the test medium comprises one or more indicators, however, these compounds may also be added during the test method. At least one indicator is present during the growth of the microorganism in the presence of the sample of the fluid in order to indicate any changes that take place in the reaction medium. The skilled artisan will appreciate that many indicators are suitable for this purpose. Particularly useful are indicators that, upon changing from one state to the other, provide a visually detectable signal such as a change in color or fluorescence. Such indicators may be easily selected from handbooks such as 'H. J. Conn's Biological Stains', R. D. Lillie ed., Baltimore, 1969. Preferred indicators are pH-indicators and/or redox indicators. Examples of suitable indicators are Acid Blue 120, Acid Orange 51, Acid Yellow 38, Alizarin acid, Alizarin Blue, Azure A, Azure B, Basic Blue 3, Brilliant Black, Brilliant Cresyl Blue, Brilliant Crocein MOO, Brilliant Yellow, Bromocresol Purple, Bromophenol Blue, Bromophenol Red, Bromothymol Blue, Congo Red, Gallocyanine, Indigo Carmine, Janus Green B, Litmus, Methylene Blue, Nile Blue A, Nitrazol Yellow (also referred to as Nitrazine Yellow), o-Nitrophenol, p-Nitrophenol, 1-10 Phenanthroline, Phenolphthalein, Safranine O, Thionin, Toluidine Blue.

In one embodiment of the first aspect of the invention, the test medium is preferably in the form of a sol or a gel. Suitable examples of gelling agents are agar, alginic acid and salts thereof, carrageenan, gelatin, hydroxypropylguar and derivatives thereof, locust bean gum (Carob gum), processed eucheuma seaweed and the like. The amount of gelling agent in the test medium is between 2 and 100 $g.l^{-1}$, preferably between 5 and 50 $g.l^{-1}$, more preferably between 10 and 20 $g.l^{-1}$, most preferably between 12 and 15 $g.l^{-1}$. However, the person skilled in the art will understand that other types of solid test media may be based on carrier materials such as ceramics, cotton, glass, metal particles, paper, polymers in any shape or form, silicates, sponges, wool and the like. In case of commercial test devices such as Premi®Test or Delvotest® the test medium is present in tubes or plates. Examples of devices useful for the purpose of the invention are transparent tubes, single or in a set or combined to a block of translucent material provided with a number of holes shaped therein. The test devices preferably have determined sizes. This is because of the reliability of the test. In case of a test based on agar diffusion technology preferably tubes are used. The test device will preferably be high enough to contain an amount of agar medium and sample corresponding to a height of 3-30 mm, more preferably 5-15 mm. The internal cross-sectional dimension of the test units is preferably 1-30 mm, more preferably 5-15 mm. The test devices are preferably closed airtight during storage, under which conditions they may be stored for at least several months. Of course any other test device suitable for executing the method of the invention is included in this invention. The volume of the agar medium in the test device is determined by the height of the test device, the internal cross-sectional dimension of the test device and the percentage of the volume of the test device, which is filled with the agar medium. The volume of the agar medium is preferably 0.01-5 ml, more preferably 0.1-1 ml. In an alternate embodiment, the test device is a plate comprising one or more wells containing the test medium. A sample of the fluid to be analyzed may be added directly to a well containing the test medium or may be added indirectly to said well, for instance by first applying the sample of the fluid to be analyzed to a carrier material such as a paper disk and then placing the carrier material onto which the fluid is adhered or absorbed onto the test medium.

In another embodiment of the first aspect of the invention, the micro-organism is a thermo stable microorganism such as a *Bacillus* species, preferably *Bacillus stearothermophilus*, or *Streptococcus* species, preferably *Streptococcus thermophilus*. These species may be introduced in the test as units capable of producing colonies, or Colony Forming Units (CFU's). Said CFU's may be spores, vegetative cells or a mixture of both. The concentration of said CFU's is expressed as Colony Forming Units per ml of test medium ($CFU.ml^{-1}$) and is usually in the range of $1\times10^5$ to $1\times10^{12}$ $CFU.ml^{-1}$, preferably $1\times10^6$ to $1\times10^{10}$ $CFU.ml^{-1}$, more preferably $2\times10^6$ to $1\times10^9$ $CFU.ml^{-1}$, most preferably $5\times10^6$ to $1\times10^8$ $CFU.ml^{-1}$, or sill more preferably $5\times10^6$ to $2\times10^7$. Examples of preferred strains are *Bacillus stearothermophilus* var. *calidolactis* C953 (deposited with the Laboratory of Microbiology of the Technical University of Delft under the accession number LMD 74.1 and with the Centraal Bureau voor Schimmelcultures (CBS), Baam under the accession number CBS 760.83) and *Streptococcus thermophilus* T101 (DSM 4022). Both strains are very sensitive to antimicrobial compounds, especially chemotherapeutics such as sulfa compounds and antibiotics such as penicillins and tetracyclines. *Escherichia coli* strains or other suitable gram-negative bacteria can be used for the detection of, for instance, quinolones. *Bacillus stearothermophilus* var. *calidolactis* C953 and *Streptococcus thermophilus* T101 are fast growing and have the advantage that they are thermophilic. For example, the optimum growth temperature of said *Bacillus* strain is between 50° and 70° C. Using thermophilic microorganisms prevents growth of the microorganism during storage or transport of the test. When the test organism is a *Bacillus* strain, it is preferably incorporated into the agar medium in the form of a spore suspension, which may be prepared and incorporated into the agar medium prior to solidification by known methods (see for example GB A 1467439). When the test organism is a *Streptococcus* strain, the bacteria are preferably incorporated into the agar medium in the form of bacterial cells, which may be prepared according to known methods (see for example EP 0285792). The concentration of the test organism in the agar medium is preferably between $10^5$ and $10^{10}$ colony forming units per ml (CFU.ml$^{-1}$) of agar medium.

In yet another embodiment of the first aspect of the invention, nutrients and/or a salt of the metal are added as a separate source, e.g. as a granulate, powder, tablet, disc or a paper filter. Also other compounds such as the indicator(s), stabilizers and/or antifolates may be added as a separate source, optionally incorporated in the nutrient medium. Suitable nutrients to enable multiplication of the test organism in the absence of antimicrobial residues are for example assimilable carbon sources (e.g. lactose, glucose or dextrose), assimilable nitrogen sources (e.g. peptone) and sources of growth factors, vitamins and minerals (e.g. yeast extract).

In a second aspect of the invention there is provided a reliable and simple method to carry out the detection of antimicrobial compounds in urine and blood. According to the invention a metal salt having a valence equal to or greater than 2 is added to the sample of fluid to be analyzed, e.g. a urine or blood sample, before adding the sample to the test system. Alternatively the test system itself may contain said metal salt as outlined in the first aspect of the invention. Unexpectedly it has been found that when a metal salt is used in the test method, the prior art problems mentioned above could be overcome with retention of the sensitivity of the test. The requirements of the metal salts, the test medium, the indicator(s), the microorganism and additional components and the preferred options are the same as outlined in the first aspect. Said metal salts are added to the test medium and/or to the sample of the fluid to be analyzed.

In one embodiment of the second aspect, the metal salt is added to the sample of the fluid to be analyzed by means of a solution, preferably an aqueous solution.

In another embodiment of the second aspect of the invention, the metal salt is added to the sample of the fluid to be analyzed in solid form. Optionally the metal salt in solid form and sample of fluid to be analyzed is mixed prior to analysis. Preferably the metal salt in solid form is added in the form of a powder, granulate, tablet, disc or paper filter. Said granulate, powder, tablet, disc or paper filter may optionally also contain nutrients and/or one or more indicators and/or stabilizers, and/or substances that change the sensitivity to certain antimicrobial compounds in a positive or negative way, and/or viscosity-increasing agents, as outlined above in the first aspect of the invention. Preferably, the concentration of said metal in said sample of fluid to be analyzed is between 0.005 and 1 M, more preferably between 0.01 and 0.1 M.

The amount of urine or blood sample to be added to the test medium depends on the test system. The test is incubated following the instructions of the producer. For microbial diffusion tests 0.01-1.0 ml, preferably 0.05-0.5 ml is added to the test medium using well-known methods. The incubation time of the test is depending on the circumstances. In case of an agar diffusion tests using *Bacillus stearothermophilus* the test is incubated in a water bath or block heater at 60-70° C., preferably at 62-65° C. Results may be obtained after 1.5-4 hours, preferably from 2.5-3.5 hours.

Any test suitable for the method of the invention is included in this invention. Examples are tests in which selected sensitive microorganisms are used, e.g. microbial agar diffusion tests, and tests based on selective binding of the compound to be detected. Selective binding can be achieved using the well-known antibody technology or by using specific tracers. Any sample of fluid is suitable for analysis by the method of the invention. It should be noted that the method of the invention is also suitable for solid substances the fluid of interest of which may be withdrawn either by diffusion, pressure or natural fluid loss. Particular examples of this latter case are meat and carrier materials that have been impregnated with the fluid to be analyzed.

In a third aspect of the invention there is provided a kit for carrying out the method of the second aspect of the present invention. Such a kit comprises one or more containers filled with test medium as described in the first aspect of the invention and a metal salt. The containers may be test tubes of any shape and size and from any material available, provided that observation of indicator changes is possible. Also, the containers may be wells such as those incorporated in micro-titer plates.

Said metal salt is a metal salt capable of forming metal ions as outlined in the first aspect of the invention. The metal salt may be present as a solution, preferably an aqueous solution, stored in a container. Preferably said metal salt is present in solid form, for example in the form of a tablet, in a disc or paper filter. The advantage of supplying the metal salt in the kit in solid form is that predetermined amounts can easily be packaged, for instance in tablets, which facilitates dosage. Yet another advantage is that the use of a metal salt in dry from does not lead to dilution of the sample and consequently to lowering of the sensitivity of the test.

Optionally, said kit comprises means for sealing of said containers filled with test medium during incubation and/or an insert with instructions for use and/or a means for setting the time needed for incubation.

In one embodiment of the third aspect, said kit comprises nutrients. Preferably said nutrients are contained within a medium such as a tablet, disc or a paper filter. Also other compounds such as the indicator(s), stabilizers and/or antifolates may be added as a separate source, optionally incorporated in the nutrient medium. When said medium is present, it is highly advantageous to also incorporate the metal salt therein.

In another embodiment of the third aspect of the present invention, said kit comprises a thermostatic device, with the aid of which test samples can be kept at a pre-set temperature. Preferably, said thermostatic device is designed in such a fashion that it can hold said containers filled with test medium. Optionally the thermostatic device is coupled to a means for setting the time needed for incubation such that heating and/or cooling is stopped after lapse of a pre-set period.

In yet another embodiment of the third aspect of the invention, said kit comprises a data carrier loaded with a computer program suitable for instructing a computer to analyze digital data obtained from a sample-reading device. Said data carrier may be any carrier suitable for storing digital information such as a CD-ROM, a diskette, a DVD, a memory stick, a magnetic tape or the like. Advantageously, said data carrier loaded with a computer program provides for easy access to the latest available computer programs suitable for use in the method of the present invention.

EXAMPLES

Example 1

Addition of Calcium Chloride ($CaCl_2$) to Urine Samples

Urine samples were examined using microbial inhibition test ampoules produced according to the methods described in EP 0005891 with the nutrients present in the agar. Said test is also known as Premi®Test (commercially available from DSM, Delft, The Netherlands).

$CaCl_2.2H_2O$ (0.81 mg, 0.0055 mmol) was dissolved in 100 µl of urine obtained from pork (a total of 10 samples was evaluated) or calves (a total of 35 samples was evaluated), which did not contain any drug residues. To the control samples no $CaCl_2$ was added. The samples were added to the test ampoules. After a pre-incubation for 20 minutes at room temperature the sample was removed and the test was incubated in a water bath at 64±1° C. following the instructions of the manufacturer. The results were obtained after 3-4 hours by reading the change of color from purple to yellow.

The results as summarized below clearly demonstrate that a treatment of the urine with $CaCl_2$ is essential to minimize false positive test results in the Premi®Test.

TABLE 1

|  | Amount of false positive results (%) | |
| --- | --- | --- |
|  | Calf | Pork |
| Urine | 60 | 10 |
| Urine + $CaCl_2$ | 9 | 0 |

Example 2

Influence of $CaCl_2$ On a Microbial Inhibition Test

Samples were examined as described in Example 1. $CaCl_2.2H_2O$ was dissolved in water or chicken meat fluid, in concentrations of 0, 0.0078, 0.0156, 0.0312, 0.0625, 0.125, 0.25, 0.5 and 1 M. The samples were added to the test ampoules. After a pre-incubation for 20 minutes at room temperature the sample was removed and the test was incubated in a water bath at 64±1° C. following the instructions of the manufacturer. The results were obtained after 165 minutes for chicken meat fluid and 185 minutes in case of water, by reading the change of color from purple to yellow. The results as summarized below clearly demonstrate that a concentration of $CaCl_2$ up to 0.25M in water does not influence the test results. In chicken meat fluid there is no inhibition in case the concentration of $CaCl_2$ is up to 1 M.

TABLE 2

|  | Color observed in microbial inhibition test | |
| --- | --- | --- |
| Concentration $CaCl_2$ (M) | Water | Chicken meat fluid |
| 0 (Control) | Yellow | Yellow |
| 0.0078 | Yellow | Yellow |
| 0.0156 | Yellow | Yellow |
| 0.0312 | Yellow | Yellow |
| 0.0625 | Yellow | Yellow |
| 0.125 | Yellow | Yellow |
| 0.25 | Yellow | Yellow |
| 0.5 | Purple | Yellow |
| 1 | Purple | Yellow |

Example 3

Addition of Calcium Chloride ($CaCl_2$) to Bovine Urine Samples

In this experiment it is demonstrated that addition of $CaCl_2$ to urine reduces the false results on a microbial inhibition test.

The samples were examined using microbial inhibition test ampoules produced according to the methods described in EP 0005891 with the nutrients present in the agar. Said test is also known as Premi®Test (commercially available from DSM, Delft, The Netherlands).

$CaCl_2.2H_2O$ (1 mg, 0.0068 mmol) was dissolved in 100 µl of urine obtained from bovine (a total of 25 samples was evaluated) which did not contain any drug residues. To the control samples no $CaCl_2$ was added. The samples were added to the test ampoules. After a pre-incubation for 20 minutes at room temperature the sample was removed and the test was incubated in a water bath at 64±1° C. following the instructions of the manufacturer. The results were obtained after 3-4 hours by reading the change of color from purple to yellow.

The results as summarized in Table 3 clearly demonstrate that a treatment of the urine with $CaCl_2$ is essential to minimize false positive test results in the Premi®Test.

TABLE 3

|  | Amount of false positive results (%) Bovine |
| --- | --- |
| Urine | 100 |
| Urine + $CaCl_2$ (1 mg/100 µl) | 12 |

Example 4

Addition of Calcium Acetate ($Ca(CH_3COO)_2$) to Bovine and Pig Urine Samples

In this experiment it is demonstrated that addition of the earth alkaline metal calcium either $CaCl_2$ or $Ca(CH_3COO)_2$ to urine reduces the false results on a microbial inhibition test.

The samples were examined using microbial inhibition test ampoules produced according to the methods described in EP 0005891 with the nutrients present in the agar. Said test is also known as Premi®Test (commercially available from DSM, Delft, The Netherlands).

$CaCl_2.2H_2O$ (1.0 mg, 0.0068 mmol), $Ca(CH_3COO)_2$ (1.0 mg, 0.0041 mmol) and $Ca(CH_3COO)_2$, (2.0 mg, 0.0082 mmol) were dissolved in 100 µl of urine obtained from bovine (a total of 25 samples was evaluated) and pig (a total of 9 samples was evaluated), which did not contain any drug residues. To the control samples no earth alkaline metal calcium was added. The samples were added to the test ampoules. After a pre-incubation for 20 minutes at room temperature the sample was removed and the test was incubated in a water bath at 64±1° C. following the instructions of the manufacturer. The results were obtained after 3-4 hours by reading the change of color from purple to yellow.

The results as summarized in Table 4 clearly demonstrate that a treatment of the urine with earth alkaline metal calcium minimize false positive test results in the Premi®Test.

TABLE 4

|  | Amount of false positive results (%) | |
| --- | --- | --- |
|  | Bovine | Pig |
| Urine | 100 | 89 |
| Urine + $CaCl_2$ (1 mg/100 µl) | 12 | 11 |
| Urine + $Ca(CH_3COO)_2$ (1 mg/100 µl) | 20 | 0 |
| Urine + $Ca(CH_3COO)_2$ (2 mg/100 µl) | 4 | 12 |

The invention claimed is:

1. Method for the determination of the presence of an antibiotic in a fluid comprising the steps of:
   (a) contacting a sample of a fluid to be tested for the presence of an antibiotic with a test medium comprising an indicator and a test microorganism which is thermostable at an incubation temperature of between 50° C. and 70° C. and is selected from the group consisting of a *Bacillus* species and a *Streptococcus* species;
   (b) incubating the test microorganism at an incubation temperature of 60° C. to 65° C. for a period of time between 1.5 to 4 hours to grow the test microorganism in case no antibiotic is present in the fluid sample; and
   (c) detecting growth or inhibition of growth of the test microorganism with the indicator, wherein
   the method further comprises adding to the test medium and/or to the sample of the fluid an alkaline earth metal salt in an amount such that the concentration of the metal in the test medium and/or the sample is between 0.005 M and 1 M.

2. Method according to claim 1, wherein the indicator is at least one pH-indicator and/or at least one redox-indicator.

3. Method according to claim 1, wherein the fluid to be tested for the presence of an antibiotic is blood, meat fluid or urine.

4. Method according to claim 1, wherein the alkaline earth metal is selected from the group consisting of calcium, barium and magnesium.

5. Method according to claim 1, wherein the concentration of said metal salt in said test medium and/or to said sample of fluid is between 0.01 and 0.1 M.

6. Method according to claim 1, wherein said metal salt is added to said sample of fluid.

7. Method according to claim 1, wherein said metal salt is added to said sample before said sample is added to said test medium.

8. Method according to claim 1, wherein said metal salt is added to said sample by means of a solution.

9. Method according to claim 1, wherein said test medium is an agar medium.

10. Method according to claim 1, wherein said test medium further comprises nutrients, stabilizers and substances that change the sensitivity to certain antimicrobial compounds in a positive or negative way and/or viscosity increasing agents.

11. Method according to claim 1, wherein step (b) is practiced at an incubation temperature of 62° C. to 65° C.

* * * * *